United States Patent
Bliweis et al.

(10) Patent No.: US 7,846,154 B2
(45) Date of Patent: Dec. 7, 2010

(54) GAS-HEATED GAS-COOLED CRYOPROBE UTILIZING ELECTRICAL HEATING AND A SINGLE GAS SOURCE

(75) Inventors: Mordechai Bliweis, Haifa (IL); Uri Amir, Or Yehuda (IL); Nir Berzak, Zikhron-Yaakov (IL); Yura Leybin, Haifa (IL); Shimon Livneh, Kiryat-Tivon (IL)

(73) Assignee: Galil Medical Ltd., Yokneam (IL)

( * ) Notice: Subject to any disclaimer, the term of this patent is extended or adjusted under 35 U.S.C. 154(b) by 1285 days.

(21) Appl. No.: 11/003,529

(22) Filed: Dec. 6, 2004

(65) Prior Publication Data

US 2006/0122590 A1 Jun. 8, 2006

(51) Int. Cl.
    *A61B 18/02* (2006.01)
(52) U.S. Cl. .......................................... 606/24; 606/21
(58) Field of Classification Search .............. 606/20–26
    See application file for complete search history.

(56) References Cited

U.S. PATENT DOCUMENTS

| | | | | |
|---|---|---|---|---|
| 3,270,744 A | * | 9/1966 | Katz | 606/25 |
| 3,298,371 A | * | 1/1967 | Lee | 606/23 |
| 3,662,755 A | | 5/1972 | Rautenbach et al. | |
| 3,910,277 A | | 10/1975 | Zimmer | |
| 3,913,581 A | | 10/1975 | Ritson et al. | |
| 3,948,269 A | | 4/1976 | Zimmer | |
| 4,018,227 A | * | 4/1977 | Wallach | 606/23 |
| 4,236,518 A | | 12/1980 | Floyd | |
| 4,377,168 A | * | 3/1983 | Rzasa et al. | 606/24 |
| 4,946,460 A | | 8/1990 | Merry et al. | |
| 5,433,717 A | * | 7/1995 | Rubinsky et al. | 606/20 |
| 5,452,582 A | | 9/1995 | Longsworth | |
| 5,522,870 A | | 6/1996 | Ben-Zion | |
| 5,632,743 A | | 5/1997 | Clarke | |
| 5,658,276 A | | 8/1997 | Griswold | |
| 5,702,435 A | | 12/1997 | Maytal | |
| 5,860,971 A | | 1/1999 | Clarke | |
| 5,899,897 A | | 5/1999 | Rabin et al. | |

(Continued)

FOREIGN PATENT DOCUMENTS

WO WO 00/59390 10/2000

*Primary Examiner*—Michael Peffley
(74) *Attorney, Agent, or Firm*—Fredrikson & Bryon, P.A.

(57) ABSTRACT

The present invention is of device, system, and method for cooling and heating an operating tip of a cryoprobe using a single source of compressed gas. Cooling of the operating tip is effected by Joule-Thomson expansion of a high-pressure cooling gas through a Joule-Thomson orifice into an expansion chamber. Heating of the operating tip is effected by electrical resistance heating. In preferred embodiments, heating of the operating tip is effected by electrical resistance heating of low-pressure gas flowing towards the operating tip. Preferably, gas from a single gas source is supplied to the probe during both cooling and heating phases, a cooling gas being supplied at high pressure when used for cooling and at low pressure when used for heating. Low-pressure gas supplied during the heating phase is heated as it flows towards the operating tip, preferably by electrical resistance heating within the body of the probe. A single gas input lumen is used during both cooling and heating phases to transport gas into the probe, and a single gas exhaust lumen is used during both cooling and heating phases to conduct gas out of the probe.

44 Claims, 5 Drawing Sheets

U.S. PATENT DOCUMENTS

| | | | |
|---|---|---|---|
| 6,007,570 A * | 12/1999 | Sharkey et al. | 607/96 |
| 6,179,831 B1 * | 1/2001 | Bliweis | 606/21 |
| 6,270,493 B1 | 8/2001 | Lalonde et al. | |
| 6,283,959 B1 * | 9/2001 | Lalonde et al. | 606/21 |
| 6,562,030 B1 * | 5/2003 | Abboud et al. | 606/21 |
| 7,240,497 B2 * | 7/2007 | Dorenkamp et al. | 62/51.1 |
| 7,294,127 B2 * | 11/2007 | Leung et al. | 606/41 |
| 2002/0049436 A1 | 4/2002 | Zvuloni et al. | |
| 2002/0188287 A1 | 12/2002 | Zvuloni et al. | |
| 2003/0014095 A1 | 1/2003 | Kramer et al. | |
| 2003/0060762 A1 | 3/2003 | Zvuloni et al. | |
| 2004/0024391 A1 | 2/2004 | Cytron et al. | |

* cited by examiner

GAS-HEATED GAS-COOLED CRYOPROBE UTILIZING ELECTRICAL HEATING AND A SINGLE GAS SOURCE

FIELD AND BACKGROUND OF THE INVENTION

The present invention relates to apparatus, system, and method for cryoablating tissues of a body. More particularly, the present invention relates to a heatable and coolable cryoprobe having an operating tip, which tip is operable to be cooled by rapid decompression of a high-pressure cooling gas expanding through a Joule-Thomson orifice, and also operable to be heated by a flow of electrically heated low-pressure cooling gas transiting that Joule-Thomson orifice.

In recent years, cryoablation of tissues has become an increasingly popular method of treatment for a variety of pathological conditions. Malignancies in body organs such as the breast, prostate, kidney, liver, and other organs are successfully treated by cryoablation, and a variety of non-malignant pathological conditions, such as benign prostate hyperplasia, benign breast-tumors, and similar growths are also well treated by cryoablation of unwanted tissues. Certain cases of intractable chronic pain are also treatable through cryosurgery, by cryoablation of selected nervous tissue.

Cryoablation of pathological tissues or other unwanted tissues is typically accomplished by utilizing imaging modalities, such as x-ray, ultrasound, CT, and MRI, to identify a locus for ablative treatment, then inserting one or more cryoprobes into that selected treatment locus, then cooling the treatment heads of the inserted cryoprobes sufficiently to cause the tissues surrounding the treatment heads to reach cryoablation temperatures, typically below about −40° C.

Tissues thus cooled are thereby caused to loose their functional and structural integrity. Cancerous cells cease growing and multiplying, and cryoablated tumor tissue materials, whether from malignant tumors or from benign growths, lose their structural integrity and are subsequently sloughed off or absorbed by the body.

One well-known technical problem in cryoablation is that when a cryoprobe is introduced into an organ or other body part and cooled to cryoablation temperatures, tissues contiguous to the cryoprobe immediately adhere to the probe, sticking to the probe as an ice cube adheres to the hand of an unwary householder using wet fingers to pick up an ice cube from his deep freeze.

Adherence of body tissues to a cryoprobe cooled to cryoablation temperatures has the effect of immobilizing that probe, which remains fixed in place until those contiguous tissues thaw and cease to adhere to the probe. Attempts to move or remove a probe by force, while body tissues adhere to the probe, risks tearing or otherwise damaging those tissues.

Adherence of tissues to operating cryoprobes is known to be a source of considerable delays in cryoablation surgery. Such delays are particularly problematic under currently preferred cryosurgery methods, which call for freezing, thawing, and refreezing of tissues, and which may utilize a given probe sequentially in a plurality of positions within an organ, during a process by which a cryoablation locus is shaped and 'sculpted' so as to encompass and destroy a lesion of known three-dimensional shape.

Consequently, currently preferred cryosurgery practice utilizes a cryoprobe which is heatable as well as coolable, thereby enabling to cool a cryoprobe to cryoablation temperatures, thereby cooling tissues surrounding that probe to cryoablation temperatures, and then to heat the probe sufficiently to thaw tissues touching the probe, thereby releasing adhesions between probe and tissue and enabling a surgeon to remove the probe, or reposition it.

Thaw heating is most typically used to free the cryoprobe from adhesion to the tissue after cryoablation, permitting rapid removal of a cryoprobe from an ablation site, thereby increasing the efficiency of, and shortening time required for, medical procedures. Thaw heating is particularly useful when it is desired to rapidly repositioning a cryoprobe for sequential use at a plurality of sites.

Certain cryoablation procedures require thaw heating as a safety precaution. In cryosurgical treatment of epicardial arrhythmia, for example, thawing may be used to protect sensitive tissues from tearing or other damage which might otherwise be caused when delicate tissues adhere to a cryoprobe held in the hands of a surgeon, where any slight unintentional movement by the surgeon risks tearing those delicate adhering tissues.

Heating is also used as a part of cryoablation procedure itself. It has been found that cycles of freezing, thawing, and re-freezing are more efficiently destructive of cell structure than is the process of freezing alone.

It is also convenient to have a cryoprobe which can be independently either heated or cooled: such multi-function probes can be used in collective probe configurations to selectively cool and ablate an ablation target using selected cooling probes, while utilizing other selected probes (possibly of identical construction, but used in heating mode) to heat other tissues which a surgeon desires to protect.

Of known heatable and coolable cryoprobe systems, the currently preferred systems utilize a dual gas supply module. Dual gas supply modules comprise a source of high-pressure cooling gas, such as argon, and a source of high-pressure heating gas, such as helium. As will be explained in further detail hereinbelow, high-pressure cooling gas, such as argon, when allowed to expand through a small (Joule-Thomson) orifice into an expansion chamber and thereby rapidly expand to a lower pressure, becomes extremely cold. Gas cooled in this manner can be used to cool the operating tip of a cryoprobe. In contrast, a high-pressure heating gas, such as helium, when allowed to expand through such an orifice becomes hotter. Gas heated in this manner is typically used to heat contemporary Joule-Thomson cryoprobes. The technology involved is set forth in U.S. Pat. No. 5,522,870 and U.S. Pat. No. 5,702,435, both entitled "Fast-changing heating-cooling device and method, to Ben-Zion Maytal.

A major advantage of Maytal's system is that the heating apparatus and the cooling apparatus of the cryoprobe are the same: a single gas input lumen, heat exchanging configuration, Joule-Thomson orifice, expansion chamber and gas output lumen can serve to cool, when a high-pressure cooling gas is supplied, and to heat, when a high-pressure heating gas is supplied. A system utilizing such a probe need only be operable to supply either a cooling gas or a heating gas, at the direction of a surgeon, as needed.

Such systems typically comprise two high pressure gas supply tanks, and sequences of one-way valves and gas control valves operable, manually or under remote control, to stop and start flows of heating or cooling gasses, as commanded by a surgeon or by a computerized command module.

Such systems, however, present a disadvantage. A dual gas supply includes two gas tanks, typically large and heavy, and a complex setup of valves and servomotors to control output from the dual gas supply, all made necessary by the need to supply two different kinds of gas, during different phases of a same surgical procedure, to a same Joule-Thomson heater/cooler.

Thus there is a widely recognized need for, and it would be highly advantageous to have, an apparatus and method providing the capabilities and advantages of fast heating and fast cooling of a cryoprobe, yet which does not require a dual gas supply system.

Prior art cryoprobes have used various additional means for heating cryprobe operating tips to facilitate disengagement of cryoprobes from frozen tissue.

U.S. Pat. No. 3,913,581 to Ritson et al. teaches configurations operable to cool an operating tip of a cryoprobe by decompressive expansion of a high-pressure gas through a Joule-Thomson orifice into an expansion chamber, and further operable to heat that operating tip by rapidly introducing high-pressure gas into that expansion chamber through a high-volume entrance to the chamber, rather than through a Joule-Thomson orifice, so that the introduced gas does not expand (decompress), but remains at, or rapidly returns to, high pressure. Riston teaches that rapid re-pressurization of the expansion chamber has the effect of causing a cooling fluid supplied as a gas to condense on cold portions of the probe thereby heating those portions.

A disadvantage of Ritson's configuration is that it fails to provide rapid and effective and sufficient heating. A further disadvantage is that Ritson's configuration requires a high-pressure valve on a high-pressure gas input line, used to switch high-pressure gas from a first gas input line (for conducting high-pressure input gas to the Joule-Thomson orifice, in cooling phase) to a second gas input line, which second line is in non-restricted fluid communication with the expansion chamber. (Ritson's second gas input line also serves as a gas exhaust line during cooling phases of operation.)

Providing the required valve inside the probe and within or near the operating tip is difficult, particularly in view of the extreme miniaturization of cryoprobes in preferred use today. Manipulating such a valve during a surgical procedure is difficult also. Providing the required valve outside the probe, on proximal portions of the gas input lines, creates a latency which causes a lagging response time when switching between heating phase and cooling phase of operation. Further, Riston's configuration calls for two gas input lumens in the cryoprobe, both strong enough to safely withstand high-pressured gas. This requirement also creates a barrier to extreme miniaturization of cryoprobes.

U.S. Pat. No. 5,338,415 to Glinka also teaches a cryoprobe having a variable gas passageway enabling gas from a gas supply line within a cryoprobe to bypass a Joule-Thomson orifice in the probe and to exhaust directly from the probe without significant decompression. In Glinka's configuration, a valve is provided for enabling most of a high-pressure input gas to rapidly traverses a gas input line and pass into a second gas exhaust path. Glinka teaches that mass flow of a high-pressure room-temperature gas which traverses most of the body of a probe without significant expansion therein is operable to heat portions of the probe. (In Glinka's configuration, most of the traversing high-pressure gas does not penetrate into the probe's expansion chamber.) Glinka's configuration is primarily used for cleaning a probe's gas supply line after cooling, but Glinka notes that continuous rapid movement of high-pressure gas through the probe will serve eventually to bring a cold probe back to room temperature.

A disadvantage of Glinka's configuration is that it too fails to provide rapid and effective and sufficient heating. A further disadvantage of Glinka's configuration is that it also requires an additional gas lumen within the body of the probe, which lumen must, like the gas input lumen common to all Joule-Thomson cryoprobes, be constructed to withstand gas input pressures which may be as high as 4000-6000 psi. The requirement for this additional high-pressure lumen is problematic in the context of the highly miniaturized cryoprobes in preferred use today.

Longsworth, in U.S. Pat. No. 5,452,582, provides yet another configuration for gas heating of a Joule-Thomson cooled cryoprobe. Longsworth's configuration provides a first gas supply line for high-pressure cooling gas, and a second gas input line into the probe for a room-temperature warming gas supplied at about 100 psi. Cooling gas supplied at high pressure through Longsworth's first gas supply line flows through a Joule-Thomson orifice to provide Joule-Thomson cooling of an operating tip of the probe. Room temperature gas supplied through Longsworth's configuration does not pass through a Joule-Thomson orifice. Passage of this room-temperature gas, bypassing the Joule-Thomson orifice, is used to heat the probe.

A disadvantage of Longsworth's configuration is that it too requires an additional gas input lumen extending into a distal portion of the cryoprobe. A probe requiring this second gas input lumen is disadvantageous in construction of a highly miniaturized cryoprobes in preferred use today.

Thus, there is a widely recognized need for, and it would be highly advantageous to have, a cryoprobe configuration which enables heating of a cryoprobe operating tip by low-pressure flow of gas, yet which does not require a plurality of gas input lines into the cryoprobe, does not require a plurality of gas inputs into an expansion chamber of that operating tip, and does not require a plurality of gas exhaust lines from that operating tip.

Further, there is a widely recognized need for, and it would be highly advantageous to have, a cryoprobe configuration which enables heating of a cryoprobe operating tip by flow of cooling gas through the probe, yet which does not require a switchable gas flow nozzle within the probe, and does provide for rapid switching from cooling to heating modes of operation.

Rabin, in U.S. Pat. No. 5,899,897 entitled "Method and apparatus for heating during cryosurgery" presents a cryoheater heated by electrical resistance heating. Rabin teaches that his cryoheater may be used in conjunction with one or more cooling cryoprobes to protect tissues in proximity to a cryoablation site. Rabin does not, however, disclose a probe operable both to heat and to cool.

Electrical heating of the external operating surfaces of a cryoprobe is not a trivial endeavor. Electrically heated surfaces must necessarily be electrically isolated from body tissues, least electric current leak into the tissues. Consequently, the probe surface in contact with body tissues cannot itself be an electrical resistance element. To heat a probe's external surface electrically, one must heat a resistance element inside the probe, and then rely on an intermediate substance to transfer heat to the external surface.

Such a process presents several problems. A heating element within an operating tip of a cryoprobe cannot be placed in direct contact with an outer (typically metallic) wall of that operating tip, since an electrical isolating layer is required to prevent current leakage from the resistance element into the tip wall and thence into body tissues. Electrical resistance elements, of course, are poor conductors of electricity, since it is the power expended across the internal resistance of such heating elements which causes the heating process. However, poor conductors of electricity are typically also poor conductors of heat. Consequently, an electrical resistance element placed in immediate proximity to an external heat-conducting wall of an operating tip of a cryoprobe will inevitably at least partially interfere with the process by which that wall is cooled, during cooling phases of utilization of the cryoprobe.

Thus, a configuration which places an electrical resistance element, and it's necessary electrical insulating layer, within or immediately contiguous to an exterior wall of a probe would enabling heating of that probe, but would also inevitably interfere with the cryoprobe cooling process. Joule-Thomson cooling takes place when a high-pressure cooling gas expands through a Joule-Thomson orifice into an expansion chamber. The expanded gas is thereby cooled to very cold temperatures. When exterior walls of that expansion chamber are also the outer walls of the cryoprobe operating tip, and those outer walls of the cryoprobe operating tip are made of a thermally conductive material, then the cold gas within the probe tip rapidly and efficiently cools the highly heat-conductive operating tip wall, which in turn rapidly and efficiently cools the surrounding tissue to cryoablation temperatures. If, however, an electrical resistance element and its necessary electrical insulation layer are interposed between the expansion chamber volume and the walls defining that volume, as would be the case if electrical resistance elements are placed within, contiguous to, or indirect contact with, those walls, then both the resistance elements themselves and their required electrically isolating layer will interfere with heat transfer between the heat-conductive outer walls and the cold gas contained in the expansion chamber volume, during cooling operation of the probe, since by their nature, electrical insulators and electrical resistance materials are poor conductors of heat.

Thus, electrical resistance elements and electrical insulating layers in proximity to external walls of the operating tip of a probe (or, alternatively, positioned within those walls) would significantly interfere with the Joule-Thomson cooling process, as described.

Consequently, there is a widely recognized need for, and it would be highly advantageous to have, a system for electrical resistance heating of a cryoprobe which does not interfere with the probe's Joule-Thomson (or other) cooling processes.

SUMMARY OF THE INVENTION

According to one aspect of the present invention there is provided a cryoprobe useable to cryoablate tissue of a body, comprising an operating tip operable to be cooled to cryoablation temperatures; and an electrical resistance heating element operable to heat the operating tip.

According to further features in preferred embodiments of the invention described below, the electrical resistance heating element is positioned within the operating tip, or is positioned within the cryoprobe and external to the operating tip.

According to still further features in the described preferred embodiments, the operating tip is operable to be cooled by expansion of high-pressure cooling gas through an orifice.

According to further features in preferred embodiments of the invention described below the electrical resistance heating element is operable to heat a flow of gas directed through a gas input lumen toward the operating tip, and may also be directed to the orifice.

According to another aspect of the present invention there is provided a cryoprobe useable to cryoablate tissue of a body, comprising an operating tip which includes a Joule-Thomson orifice, the operating tip is operable to be cooled by expansion of high-pressure cooling gas through the orifice, and the operating tip further comprises an electrical resistance heating element.

According to yet another aspect of the present invention there is provided a cryoprobe having an operating tip operable to be cooled by expansion of high-pressure cooling gas expanding through a Joule-Thomson orifice, and also operable to be heated by a flow of heated low-pressure cooling gas transiting that orifice.

According to still another aspect of the present invention there is provided a cryoprobe useable to cryoablate tissue of a body, comprising an operating tip which includes a Joule-Thomson orifice, which operating tip is operable to be cooled by expansion of high-pressure cooling gas through that orifice, and wherein the operating tip is further operable to be heated by flowing heated low-pressure gas directed to that operating tip.

According to further features in preferred embodiments of the invention described below, a common gas input lumen is operable to deliver both high-pressure gas and low pressure gas to that operating tip. The common gas input lumen may also be is operable to deliver both high-pressure gas and low-pressure gas to the orifice.

Preferably, the cryoprobe further comprises a gas input lumen and an electrical resistance heating element proximate to a portion of the gas input lumen, and an electrical resistance heating element operable to heat gas flowing within the gas input lumen. The probe may also comprise a thermal sensor, which may be a thermocouple.

The cryoprobe may comprise an electrical resistance heating element operable to heat a flow of low-pressure gas.

According to still further features in the described preferred embodiments, the cryoprobe comprises a heat-exchanging configuration which comprises an electrical resistance heating element. The heat-exchanging configuration may comprise a gas input lumen spirally wrapped around a central core, and that central core may comprise an electrical resistance heating element. Alternatively, the cryoprobe may comprise a gas exhaust lumen containing an electrical resistance heating element and a portion of a gas input lumen. Alternatively, the cryoprobe may comprise a gas exhaust lumen, a gas input lumen at least a portion of which is contained within the gas exhaust lumen, and an electrical resistance heating element external to, and contiguous to, the gas exhaust lumen.

According to an additional aspect of the present invention there is provided a cryoprobe comprising a gas input lumen operable to direct high-pressure gas to a Joule-Thomson orifice; and an electrical resistance heating element operable to heat a low-pressure gas directed through the gas input lumen to the orifice.

According to yet an additional aspect of the present invention there is provided a system for cryoablating tissue, comprising a cryoprobe useable to cryoablate tissue of a body, which cryoprobe comprises an operating tip which includes a Joule-Thomson orifice, which operating tip is operable to be cooled by expansion of high-pressure cooling gas through said orifice, and wherein the operating tip is further operable to be heated by flowing heated low-pressure gas directed to the operating tip. The system further comprises a gas supply operable to supply high-pressure cooling gas to the cryoprobe and also operable to supply low-pressure cooling gas to the cryoprobe; and a power supply operable to supply electric power to a resistance element operable to heat a flow of low-pressure cooling gas.

According to still further features in the described preferred embodiments the resistance element is positioned within the cryoprobe, and may be positioned within the operating tip, optionally within an expansion chamber contiguous to the orifice. The system may further comprise a heat exchanging configuration which comprises that resistance element. The gas supply may be further operable to supply high-pressure heating gas to the cryoprobe.

Preferably, the system comprises a control module operable to influence temperatures of the cryoprobe by regulating output of at least one of a group consisting of the power supply and the gas supply.

Preferably, the control module is operable to influence temperatures of the cryoprobe by regulating output of the power supply and by regulating output of the gas supply.

The system may further comprise a current sensor and a power cut-off switch operable to cut power to the resistance element when current detected by the current sensor indicates that the resistance element has heated beyond a predetermined threshold. The power cut-off switch may be operable to cut power to the resistance element when current detected by the current sensor falls below a predetermined threshold.

The control system is preferably operable to calculate an operational command for the power supply based on algorithmic analysis of data obtained from a thermal sensor, which may be a thermocouple, or from a pressure sensor, or from a current sensor, or from a gas flow sensor, which gas flow sensor may comprise an electrical resistance heating element whose resistance varies as a function of its temperature, and a current sensor operable to measure current flowing through that electrical resistance heating element.

According to still further features in the described preferred embodiments the cryoprobe is constructed of MRI-compatible material such as titanium or inconel, and electrical components within and proximate to the cryoprobe are shielded with Mu-metal.

According to yet an additional aspect of the present invention there is provided a method for using a cryoprobe to cryoablate tissues at a cryoablation target site within a body and for subsequently disengaging that cryoprobe from the cryoablation site, the method comprising positioning an operating tip of the cryoprobe in a vicinity of a cryoablation target site, cooling the operating tip to cryoablation temperatures, thereby cryoablating tissues at the cryoablation target site, and utilizing an electrical resistance heating element within the cryoprobe to heat the operating tip, thereby thawing tissues contiguous to the operating tip, thereby cryoablating tissue at the cryoablation target site and subsequently disengaging the cryoprobe from the cryoablation target site.

Preferably, the method further comprises utilizing the electrical resistance heating element to heat a flow of gas directed through a gas input lumen to the operating tip, and preferably to a Joule-Thomson orifice in that operating tip.

According to still an additional aspect of the present invention there is provided a power cut-off system for a cryoprobe, comprising an electrical resistance heating element for heating an operating tip of a cryoprobe, a current detector operable to report a measure of current passing through the electrical resistance heating element when the electrical resistance heating element is used to heat the operating tip, a power supply operable to supply power to the electrical resistance heating element; and a power cut-off switch operable to cut off power flow from the power supply to the electrical resistance element when the current detector detects a current inferior to a predetermined value.

The present invention successfully addresses the shortcomings of the presently known configurations by providing a cryoprobe having the capabilities and advantages of fast heating and fast cooling, yet which does not require a dual gas supply system.

The present invention further successfully addresses the shortcomings of the presently known configurations by providing a cryoprobe operable to heat a cryoprobe operating tip by low-pressure flow of gas, yet which does not require a plurality of gas input lines into the cryoprobe, does not require a plurality of gas inputs into an expansion chamber of that operating tip, and does not require a plurality of gas exhaust lines from that operating tip.

The present invention further successfully addresses the shortcomings of the presently known configurations by providing a cryoprobe operable to heat a cryoprobe operating tip by flow of cooling gas through the probe, yet which does not require a switchable gas flow nozzle within the probe, and does provide for rapid switching from cooling to heating modes of operation.

The present invention further successfully addresses the shortcomings of the presently known configurations by providing a cryoprobe heatable by electrical resistance heating, wherein electrical resistance heating elements do not interfere with the probe's cryogenic cooling processes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of a heatable and coolable cryoprobe, a cryoprobe system, and cryoablation method, wherein a cryoprobe having an operating tip coolable by Joule-Thomson cooling is heatable by electrical resistance heating. Specifically, during a cooling phase of operation an operating tip of a cryoprobe of the present invention is cooled by Joule-Thomson expansion of high-pressure cooling gas from a high-pressure cooling gas supply, enabling cryoablation of body tissues. During a heating phase of operation, electrical resistance heating is used to heat the probe, preferably by heating low-pressure cooling gas supplied by the high-pressure cooling gas supply and a pressure regulator, which gas is heated while flowing towards the operating tip, thereby heating the operating tip and facilitating disengagement of the probe from cryoablated tissues.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

To enhance clarity of the following descriptions, the following terms and phrases will first be defined:

The phrase "heat-exchanging configuration" is used herein to refer to component configurations traditionally known as "heat exchangers", namely configurations of components situated in such a manner as to facilitate the passage of heat from one component to another. Examples of "heat-exchanging configurations" of components include a porous matrix used to facilitate heat exchange between components, a structure integrating a tunnel within a porous matrix, a structure including a coiled conduit within a porous matrix, a structure including a first conduit coiled around a second conduit, a structure including one conduit within another conduit, or any similar structure.

The phrase "Joule-Thomson heat exchanger" as used herein refers, in general, to any device used for cryogenic cooling or for heating, in which a gas is passed from a first region of the device, wherein it is held under higher pressure, to a second region of the device, wherein it is enabled to expand to lower pressure. A Joule-Thomson heat exchanger may be a simple conduit, or it may include an orifice, referred to herein as a "Joule-Thomson orifice", through which gas passes from the first, higher pressure, region of the device to the second, lower pressure, region of the device. A Joule-Thomson heat exchanger may further include a heat-exchanging configuration, for example a heat-exchanging configuration used to cool gasses within a first region of the device, prior to their expansion into a second region of the device.

It is to be noted that the phrase "Joule-Thomson orifice" is used herein to refer to an orifice used, during a first phase of operation of a device, as described in the preceding paragraph (that is, an orifice used as a conduit for gas transiting from a high-pressure to a low-pressure region of a device), even though that orifice may be used differently, or not used at all, during a second phase of operation of that device. For simplicity of exposition, an orifice used during some phase of operation of a device as a conduit for gas transiting from a high-pressure to a low-pressure region of that device will be referred to throughout as a Joule-Thomson orifice, even though, strictly speaking, that orifice functions is a "Joule-Thomson orifice" (in the traditional sense of that term) only during its use as a transition conduit from high to low-pressure regions. Thus, an orifice used as a Joule-Thomson orifice (in the traditional sense of the term) during cooling phases of operation of a cryoprobe, and used as a conduit for low-pressure gas during a heating phase of operation of that cryoprobe, will, for simplicity, be referred to herein as a "Joule-Thomson orifice".

The phrase "cooling gasses" is used herein to refer to gasses which have the property of becoming colder when passed through a Joule-Thomson heat exchanger. As is well known in the art, when gasses such as argon, nitrogen, air, krypton, $CO_2$, $CF_4$, and xenon, and various other gasses pass from a region of higher pressure to a region of lower pressure in a Joule-Thomson heat exchanger, these gasses cool and may to some extent liquefy, creating a cryogenic pool of liquefied gas. This process cools the Joule-Thomson heat exchanger itself, and also cools any thermally conductive materials in contact therewith. A gas having the property of becoming colder when passing through a Joule-Thomson heat exchanger is referred to as a "cooling gas" in the following.

The phrase "heating gasses" is used herein to refer to gasses which have the property of becoming hotter when passed through a Joule-Thomson heat exchanger. Helium is an example of a gas having this property. When helium passes from a region of higher pressure to a region of lower pressure, it is heated as a result. Thus, passing helium through a Joule-Thomson heat exchanger has the effect of causing the helium to heat, thereby heating the Joule-Thomson heat exchanger itself and also heating any thermally conductive materials in contact therewith. Helium and other gasses having this property are referred to as "heating gasses" in the following.

As used herein, a "Joule Thomson cooler" is a Joule Thomson heat exchanger used for cooling. As used herein, a "Joule Thomson heater" is a Joule Thomson heat exchanger used for heating.

The term "ablation temperature", as used herein, is the temperature at which cell functionality and structure are destroyed by cooling. Temperatures below approximately −40° C. are generally considered to be ablation temperatures.

As used herein, the term "high-pressure" as applied to a gas is used to refer to gas pressures appropriate for Joule-Thomson cooling of cryoprobes. In the case of argon gas, for example, "high-pressure" argon is typically between 3000 psi and 4500 psi, though somewhat higher and lower pressures may sometimes be used.

As used herein, the term "low-pressure" as applied to a gas is used to refer to gas pressures above atmospheric pressure, yet low enough so that decompression of a cooling gas at "low pressure" to near atmospheric pressure will not result in radical cooling of that gas. In the case of argon, gas pressurized to between 200 psi and 1000 psi would be considered "low pressure" gas. Pressures of between 300 psi and 600 psi are currently recommended for the uses of "low pressure" gas disclosed hereinbelow.

It is expected that during the life of this patent many relevant cryoprobes will be developed, and the scope of the term "cryoprobe" is intended to include all such new technologies a priori.

As used herein the term "about" refers to ±10%.

In discussion of the various figures described hereinbelow, like numbers refer to like parts.

Preferred embodiments of the present invention present device, system, and method for cooling and heating an operating tip of a cryoprobe using a single source of compressed gas. Cooling of the operating tip is effected by Joule-Thomson expansion of a high-pressure cooling gas through a Joule-Thomson orifice into an expansion chamber. Heating of the operating tip is accomplished by electrical resistance heating. In a preferred embodiment, heating of the operating tip is accomplished by electrical resistance heating of low-pressure gas flowing towards the operating tip. Preferably, gas from a single gas source is supplied to the probe during both cooling and heating phases, the gas being supplied at high pressure when used for cooling and at low pressure when used for heating. Low-pressure gas supplied during the heating phase is heated during its passage towards the operating tip, preferably by electrical resistance heating within the body of the probe. Preferably, a common single gas input lumen and a single gas exhaust lumen are used during both cooling and heating phases to transport gas into the probe, to and through an orifice, and back out of the probe.

A system utilizing the cryoprobe described in the preceding paragraph comprises that probe, a gas supply module, a power supply module, and a control module.

The gas supply module is operable to supply gas at a selected pressure. The gas supply module is operable, during cooling phases of operation of the system, to supply cooling gas at a high-pressure, which gas and pressure are appropriate for cooling an operating tip of the probe by Joule-Thomson effect when that high-pressure cooling gas expands into an expansion chamber upon passage through a Joule-Thomson orifice in the operating tip.

The gas supply module is further operable, during a heating phase of use of the system, to supply cooling gas (or less preferably, any other gas) at a pressure low enough to avoid substantial Joule-Thomson cooling of the gas, yet high enough to cause gas to flow towards and through the operating tip of the probe.

During heating phases of operation, electrical resistance heating is used to heat an operating tip of the probe, preferably by heating low-pressure gas supplied by the gas supply module and flowing towards the operating tip of the probe.

A power supply module is operable to supply electric power to one or more electrical heating elements within the probe, as required to produce and maintain a desired temperature within the probe.

Preferably, the system comprises a control module operable to receive information from temperature sensors and/or pressure sensors positioned within the probe or in other parts of the system. Preferably, the control module is operable to receive commands from a surgeon and/or from an algorithmic control program, and is operable to control heating and cooling of the probe by regulating flow of gas towards the probe, pressure of the supplied gas, and/or supply of power to heating elements of the probe. Preferably, feedback information from the sensors is used by the control module to maintain a desired temperature profile within the operating tip of the cryoprobe during various phases of operation.

Figure 1:
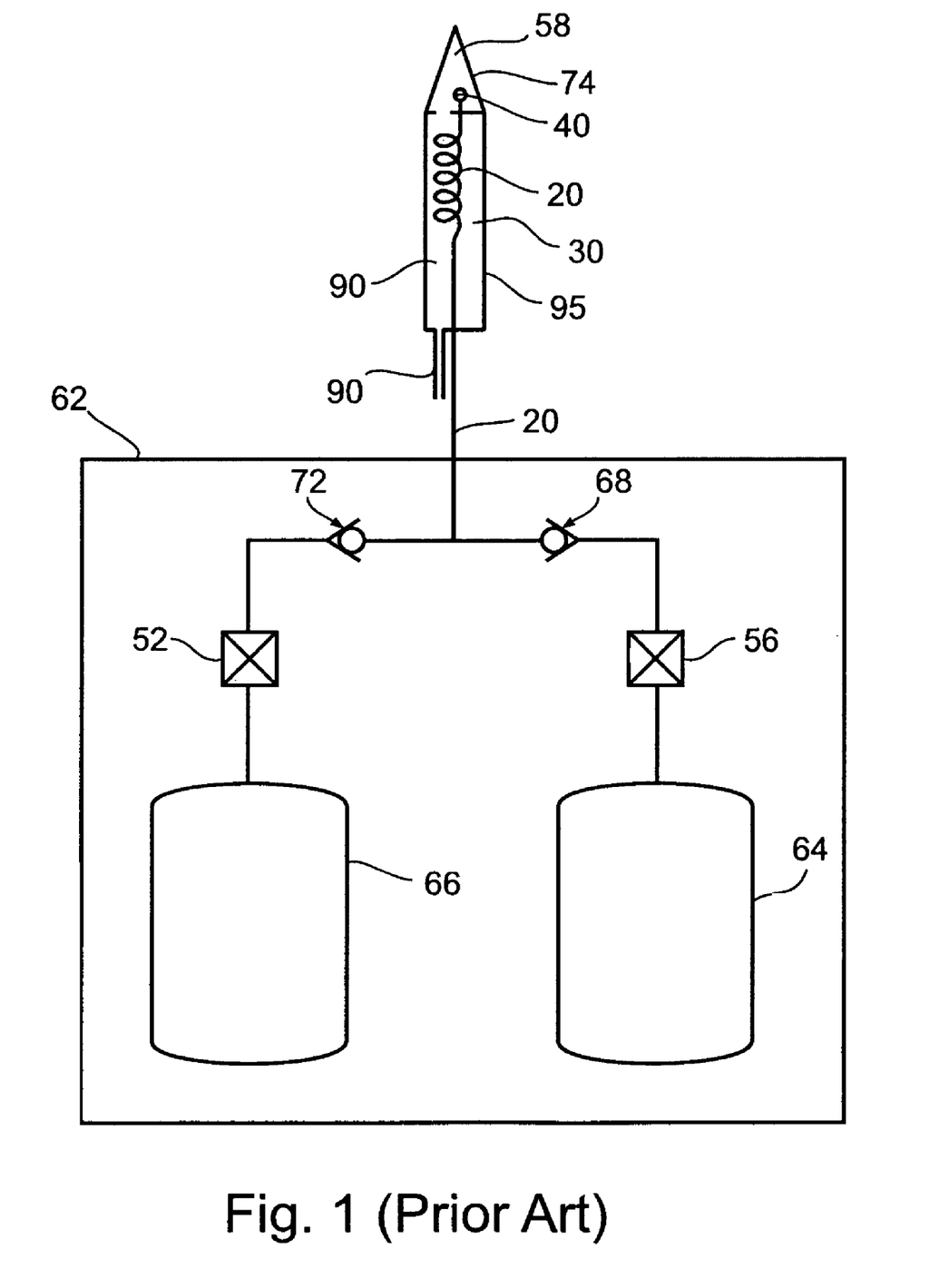
FIG. 1 is a simplified schematic of a cryoprobe system including a Joule-Thomson heatable and Joule-Thomson coolable cryoprobe and a dual high-pressure gas supply, according to methods of prior art.

For purposes of better understanding the present invention, as illustrated in FIGS. 1-8 of the drawings, reference is first made to the construction and operation of a conventional (i.e., prior art) cryoprobe system as illustrated in FIG. 1.

FIG. 1 is a simplified schematic of a cryoprobe system including a Joule-Thomson heatable and Joule-Thomson coolable cryoprobe and a dual high-pressure gas supply, according to methods of prior art.

FIG. 1 presents, in very simplified schematic, a probe 95 having a gas input lumen 20, a gas exhaust lumen 90, a Joule-Thomson orifice 40 operable to receive a gas supplied through gas input lumen 20 and to permit passage of that gas through orifice 40 into an expansion chamber 58. Gas released into expansion chamber 58 exhausts through gas exhaust lumen 90. In the embodiment shown in FIG. 1, gas input lumen 20 is partially positioned within gas exhaust lumen 90, thereby created a heat exchanging configuration 30.

A dual gas supply module 62 includes a cooling gas supply 64 and a heating gas supply 66. Flow of gas from cooling gas supply 64 into probe gas input lumen 20 is controlled by on-off valve 56 and one-way valve 68. Flow of gas from heating gas supply 66 is controlled by on-off valve 52 and one-way valve 72.

When it is desired to cool tissues, valve 56 is opened and valve 52 is closed, allowing passage of high-pressure cooling gas from cooling-gas supply 64 to flow through gas input lumen 20 to orifice 40, to expand therethrough into expansion chamber 58, thereby cooling that gas and consequently cooling wall 74 of robe 95. Tissues adjacent to walls 74 are cooled when walls 74 are cooled.

When it is desired to heat tissues, valve 56 is closed and valve 52 is opened, allowing passage of high-pressure heating gas from heating-gas supply 66 to flow through gas input lumen 20 to orifice 40, to expand therethrough into expansion chamber 58, thereby heating that gas and consequently heating walls 74. Tissues adjacent to walls 74 are heated when walls 74 are heated.

It is to be noted that during a cooling phase of operation, cold expanded cooling gas exhausts from chamber 58 through gas exhaust lumen 90. In heat exchanging configuration 30 heat is transferred from gas contained in gas input lumen 20 to cold exhausting gasses contained in gas exhaust lumen 90, which cold exhausting gasses were cooled by expansion in expansion chamber 58. Heat exchange in heat exchanging configuration 30 thus pre-cools high-pressure cooling gas contained in gas input lumen 20.

Similarly, during a heating phase of operation, hot expanded heating gas exhausts from chamber 58 through gas exhaust lumen 90. In heat exchanging configuration 30 heat is transferred from hot exhausting gasses flowing through gas exhaust lumen 90 (which hot exhausting gasses wee heated by expansion in expansion chamber 58) to gasses in gas input lumen 20, thereby pre-heating high-pressure heating gas contained in gas input lumen 20.

As has been explained in the background section above, preferred contemporary cryosurgical techniques often require that cryoprobes first be cooled to cryoablation temperatures to cryoablate tissues, and then be heated to thaw tissues contiguous to the probe, thereby releasing adhesions between the probe and frozen tissues contiguous thereto.

In the prior art technology presented in FIG. 1, probe 95 is heated when valve 52 allows gas supply 66 to supply a high-pressure heating gas such as helium to gas input lumen 20 of probe 95. Valves 52 and 56 enable to manually or automatically switch between supply of high-pressure cooling gas and high-pressure heating gas thereby enabling to alternate between Joule-Thomson cooling of probe 95 and Joule-Thomson heating of probe 95.

Figure 2:
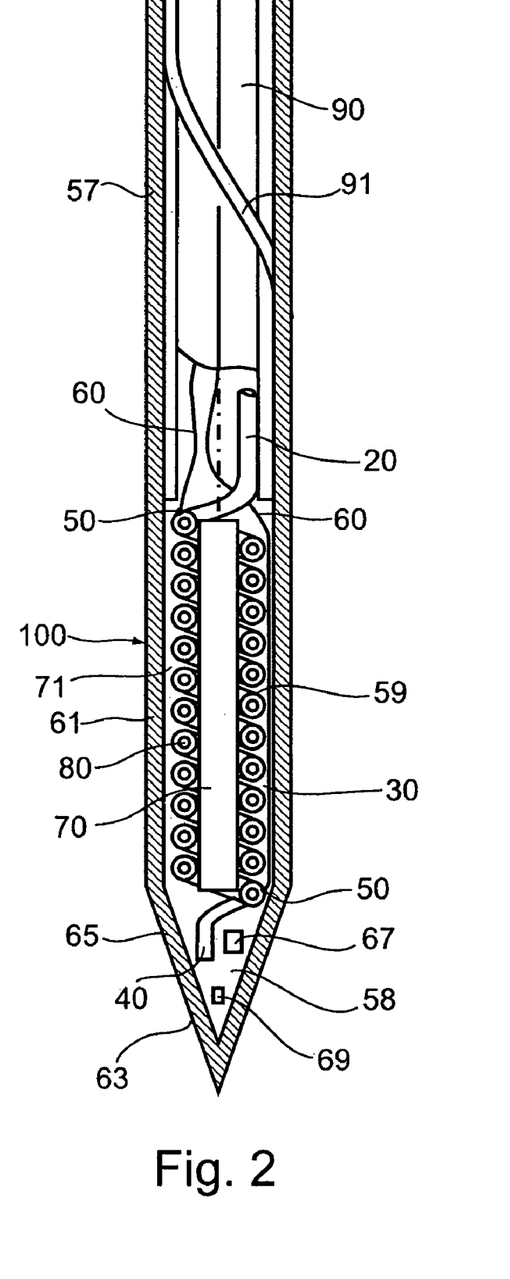
FIG. 2 is a simplified schematic of a heatable/coolable cryoprobe, according to an embodiment of the present invention.

Attention is now drawn to FIG. 2, which is a simplified schematic of a heatable/coolable cryoprobe 100, according to an embodiment of the present invention.

Cryoprobe 100 receives input gas through gas input lumen 20. A portion 59 of gas input lumen 20 is formed as a spirally wrapped coil wrapped around a central core 70. Central core 70 serves primarily as a physical support for spirally wrapped portion 59 of gas input lumen 20.

Gas input lumen 20 terminates in a Joule-Thomson orifice 40, whence in-flowing gas passes into an expansion chamber 58.

Gas exhausts from chamber 58 by passing through a volume 71 defined by the interior of distal walls 61 of cryoprobe 100 and the exterior of central core 70 of probe 100. Volume 71 also contains spirally wrapped portion 59 of input lumen 20. Thus, gas exhausting from chamber 58 passes over and around the exterior of spirally wrapped portion 59 of input lumen 20. The described configuration within volume 71 thus constitutes a heat-exchanging configuration 30, wherein, during operation of probe 100, temperature of input gas contained within input lumen 20 is influenced by temperature of gasses exhausting from chamber 58.

Thus, if high-pressure cooling gas is supplied in input lumen 20 and passes through orifice 40 into chamber 58 where it is enabled to expand, expansion of that cooling gas cools the gas, which in turn cools walls 65 of expansion chamber 58. Cooled cooling gas then flows through heat-exchanging configuration 30, flowing over the exterior of spirally wrapped portion 59 of input gas lumen 20, thereby cooling distal walls 61, which are adjacent to heat exchanging configuration 30, and also pre-cooling incoming cooling gas flowing through spirally wrapped portion 59 of gas input lumen 20 towards orifice 40. To enhance exchange of heat in heat exchanging configuration 30, spirally wrapped portion 59 of input lumen 20 is preferably constructed of heat-conductive material formed with flanges to increase surface of contact between portion 59 of input lumen 20 and exhaust gasses passing over its exterior surface, thereby enhancing heat exchange between gasses inside portion 59 of input lumen 20 and exhaust gasses passing over the exterior of portion 59 of input lumen 20.

Walls 65 of expansion chamber 58, expansion chamber 58, orifice 40, and distal walls 61 adjacent to heat exchanging configuration 30 together form operating tip 63 of probe 100. Operating tip 63 is that portion of probe 100 which cools to cryoablation temperatures when probe 100 is operated in cooling mode. (Cooling gas expanding in expansion chamber 58 is coldest in expansion chamber 58, and warms somewhat as it flows through heat exchanging configuration 30.)

Exhausting gas, having passed through heat exchanging configuration 30, subsequently passes into gas exhaust lumen 90, and thence out of probe 100. As may be seen in FIG. 2, gas input lumen 20 is preferably positioned within gas exhaust lumen 90, which positioning enables and facilitates further heat exchange between incoming gas in gas input lumen 20 and exhausting gas in gas exhaust lumen 90. A separator 91 loosely wrapped around gas exhaust lumen 90 provides separation between gas exhaust lumen and medial walls 57 of probe 100, thereby insulating medial walls 57 from gas exhaust lumen 90, which becomes cold during cooling operation of probe 100. Further, flanges are provided to direct gas exhausting from heat exchanging configuration 30 into gas exhaust lumen 90, so that no exhausting gas can pass between gas exhaust lumen 90 and medial walls 57. Consequently, distal walls 61 of probe 100 become cold during cooling operation of probe 100, but medial walls 57 do not become dangerously cold. Thus, tissues contiguous to medial portions of probe 100 are protected from harm while tissues contiguous to distal portions of probe 100 (i.e. tissues contiguous to operating tip 63 of probe 100) are cryoablated.

Thus, in a manner similar to that described with respect to the prior art cryoprobe presented in FIG. 1, if high-pressure cooling gas is supplied in input lumen 20 of probe 100, Joule-Thomson cooling of operating tip 63 of probe 100 results, and heat-exchanging configuration 30 serves to pre-cool that incoming cooling gas. Similarly, if high pressure heating gas is supplied in gas input lumen 20 of probe 100, then Joule-Thomson heating of operating tip 63 of probe 100 results, and heat exchanging configuration 30 serves to pre-heat that incoming heating gas. Thus, probe 100 can function as a prior art cryoprobe similar to that described in FIG. 1, if supplied with high-pressure cooling gas for cooling and with high-pressure heating gas for heating.

Figure 3:
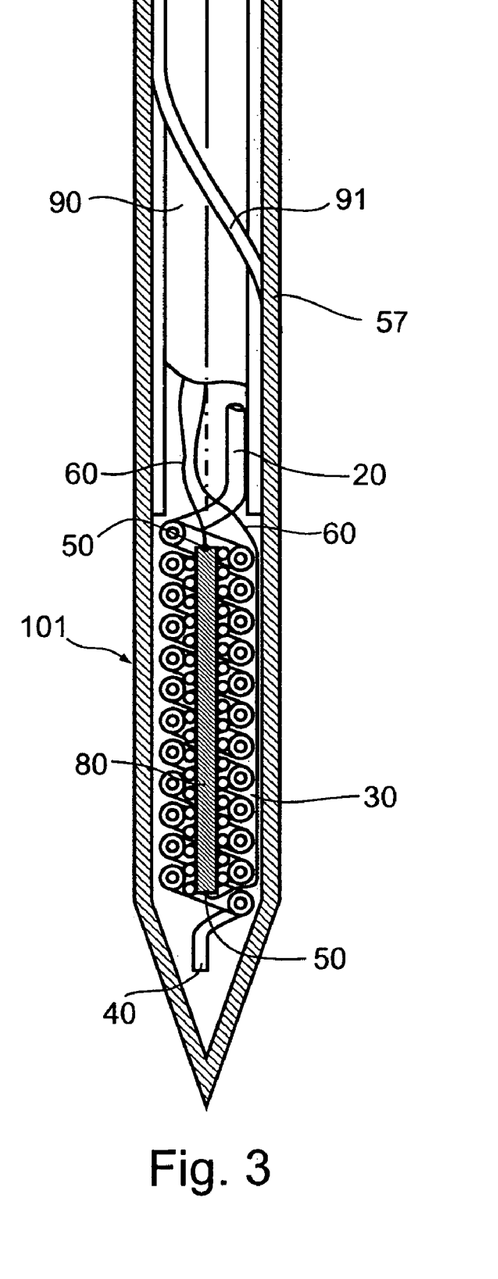
FIG. 3 is a simplified schematic of cryoprobe according to an alternative embodiment of the present invention.
Figure 4:
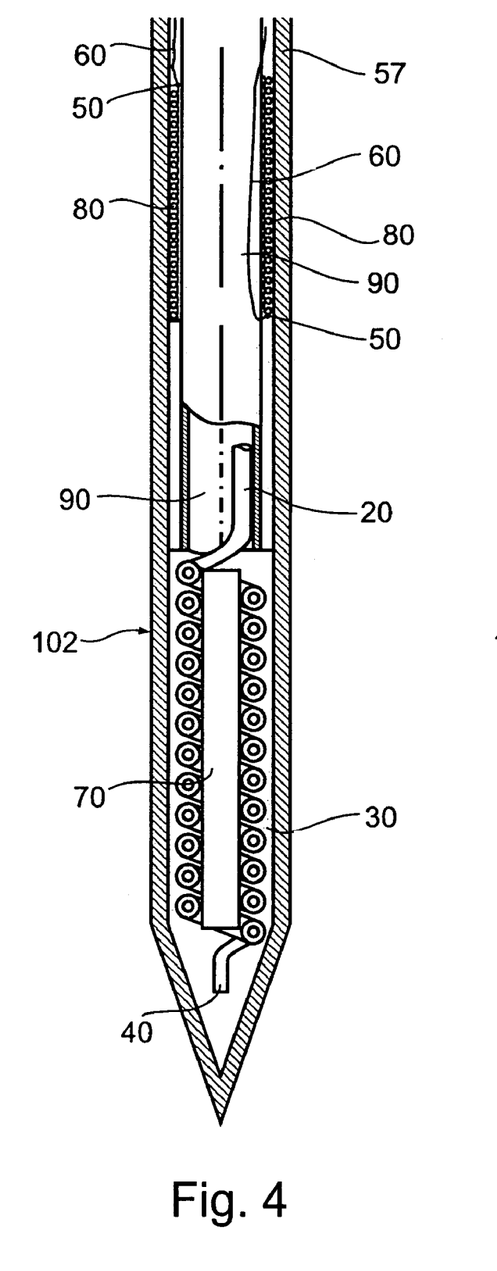
FIG. 4 is a simplified schematic of a cryoprobe according to an additional alternative embodiment of the present invention.
Figure 5:
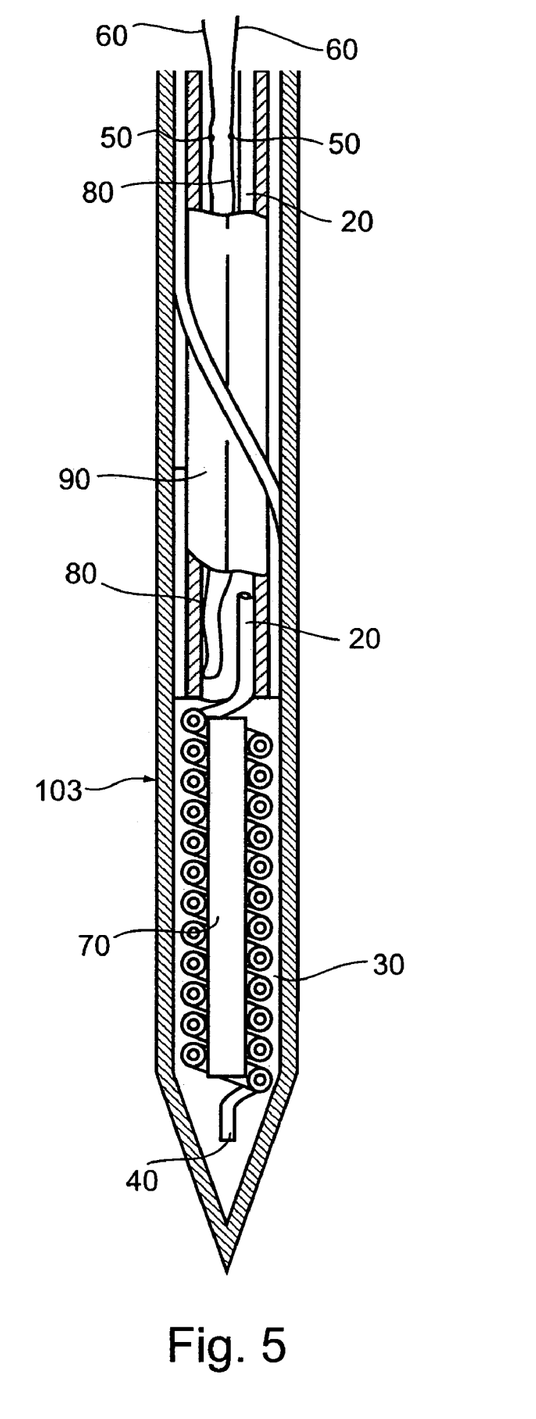
FIG. 5 is a simplified schematic of a cryoprobe according to yet another alternative embodiment of the present invention.

However, probe 100, and probes presented hereinbelow with reference to FIGS. 3, 4, and 5, are distinguished from probes constructed according to methods of prior art by presence of an electrical resistance heater within probe 100.

According to a preferred embodiment presented in FIG. 2, spirally wrapped portion 59 of gas input lumen 20 is formed of electrical resistance material appropriate for electrical resistance heating. Power leads 60 are connected at connection points 50 to one and another end of spirally wrapped portion 59 of gas input lumen 20. During cooling phases of operation of probe 100 no power is supplied to power leads 60, and cooling of probe 100 proceeds as described above. During heating phases of operation of probe 100, power is supplied across power leads 60, causing portion 59 of input lumen 20 to function as an electrical resistance heater 80, thereby heating gas flowing within gas input lumen 20, and also heating exhaust gasses passing through heat exchanging configuration 30 external to portion 59 of input lumen 20. Heated gas thus created during heating phase of operation of probe 100 serves to heat operating tip 63 of probe 100.

In a preferred mode of use, low-pressure gas is supplied through gas input lumen 20 during heating phases of operation of probe 100. Thus, a constant low-pressure flow of gas passes both within and without spiral portion 59 of gas input lumen 20, while (during heating phase of operation), spiral portion 59 functions as electrical resistance heater 80.

Low-pressure gas of between 300-600 psi has been found to be appropriate for use during heating phases of operation of probe 100, this pressure being required to produce adequate gas flow through the necessarily small aperture of orifice 40. Low-pressure gas thus supplied will consequently undergo some expansion when passing through orifice 40, yet does not undergo major expansion comparable to that experienced by high-pressure gas transiting orifice 40. Consequently, whatever cooling takes place as low-pressure gas transits orifice 40 can easily be compensated by pre-heating of that gas in gas input lumen 20, or by electrical heating of the flowing gas in expansion chamber 58 as described below. Consequently, low-pressure gas flow required for heating-phase operation of probe 100 can be supplied in the form of low-pressure cooling gas, such as argon, supplied in gas input lumen 20. Low-pressure cooling gas so supplied undergoes slight cooling as it transits orifice 40, which slight cooling effect is easily offset by pre-heating of that low-pressure cooling gas in gas input lumen 20, as described above. It is convenient to use low-pressure cooling gas during heating phases of operation, and high-pressure cooling gas during cooling phases of operation, since a single gas source, with a switchable pressure regulator, can supply gas needed both during cooling and during heating of probe 100, thus providing great simplicity in construction, maintenance, and operation of the device.

Alternatively, any other low pressure gas (e.g., air) can be supplied through gas input lumen 20 during heating phase of operation.

Further alternatively, no gas flow may be supplied in input lumen 20 during a heating phase of operation of probe 100. Electrically heating probe 100 without gas flow has an advantage of simplicity, since no provision for supplying low-pressure gas is required.

In an optional configuration particularly useful for heating probe 100 without gas flow, an expansion chamber heater 67 is provided within expansion chamber 58. Expansion chamber heater 67 is an electrical resistance heater (electrical connections not shown in the figure), preferably positioned at a distance from walls 65 of expansion chamber 58, so as to avoid interfering with cooling of walls 65 during cooling phases of operation of probe 100. During cooling phases of operation of probe 100, high-pressure cooling gas flows through input lumen 20, and operating tip heater 67 is inactive. During heating phases of operation of probe 100, and particularly if no gas flows though input lumen 20, expansion chamber heater 67 receives electrical power, causing it to heat, and thereby to heat residual gas within chamber 58, thereby heating walls 65 of chamber 58, which are exterior walls of operating tip 63.

However, electrical heating of static gasses tends to create stratification of layers of gas with different temperatures within probe 100, hot gas standing near the electrical heating elements and a cold boundary layer forming near the probe walls, with only limited tendency for mixing of those stratified layers. Therefore, heating probe 100 by electric resistance heating of a low-pressure gas flowing within probe 100 is a presently preferred mode of operation, since flowing heated gas provides superior distribution of heat and superior conduction of heat to external walls of operating tip 63. During low-pressure gas-flow heating, optional expansion chamber heater 67 may also be used as a supplement to, or in place of, heater 80 described hereinabove. Low-pressure gas flowing into expansion chamber 58 creates gas circulation and/or turbulence within chamber 58, thereby enhancing transfer of heat from heater 67 to walls 65 of chamber 58.

Preferably, electric heating of low-pressure gas during heating phases of operation is monitored by a thermal sensor 69, which may be a thermocouple. Gas flow rates in lumen 20 and levels of power supplied across power leads 60 may both be adjusted, so as to control and manage heating of operating tip 63.

As mentioned above, in a particularly preferred implementation, low pressure cooling gas is supplied through input lumen 20 during heating phases of operation of probe 100. In this implementation, cooling gas is supplied at a pressure low enough to prevent significant Joule-Thomson cooling of that gas as it passes through orifice 40, yet at a pressure sufficient to provide gas flow through input lumen 20 towards operating tip 63. Use of cooling gas in this context provides great advantages of simplicity in construction and use of a gas supply module used to supply gas to cryoprobe 100, since a single gas source can then be used to supply gas during both cooling phases and heating phases of operation of probe 100.

Attention is now drawn to FIG. 3, which presents a simplified schematic of an alternative preferred embodiment of the present invention, labeled cryoprobe 101. Construction and operation of cryoprobe 101 is in all respects similar to that of cryoprobe 100 as described in the preceding paragraph, except that in cryoprobe 101 electrical resistance heating is provided by an electrical resistance heater 80 in central core 70, portion 59 of input lumen 20 being spirally wound around central core 70 as described above with respect to cryoprobe 100. Central core 70 may contain an electrical resistance heater 80, but in a preferred embodiment central core 70 is itself an electrical resistance heater 80. That is, central core 70 may be constructed of electrical resistance material, and be connected to power leads 60 at connection points 50 as shown in FIG. 3. During heating phases of operation of probe 101, power is delivered to power leads 60, causing heating of central core 70, thereby heating in flowing low-pressure gas passing through portion 59 of input lumen 20 towards operating tip 63, thereby warming operating tip 63.

Attention is now drawn to FIG. 4, which presents a simplified schematic of an additional alternative embodiment of the present invention, labeled cryoprobe 102. Construction and operation of cryoprobe 102 is similar to that described in the preceding paragraph, with the exception that in cryoprobe 102 electrical resistance heating is provided by an electrical resistance coil 80 positioned proximal to heat exchanging configuration 30. In FIG. 4, an electrical resistance heating element is formed as a resistance coil wrapped around gas exhaust lumen 90 positioned in a medial portion of cryoprobe 102, as shown. Gas exhaust lumen 90 contains a medial portion of gas input lumen 20, consequently electrical heating of resistance coil 80 can heat gas exhausting through gas exhaust lumen 90, which in turn heats that portion of gas input lumen 20 contained within gas exhaust lumen 90, thereby heating input gas contained within gas input lumen 20. Heated gas from lumen 20 then heats operating tip 63. In this embodiment, resistance heating element 80 serves in place of separating element 91 (shown in FIGS. 2 and 3) to separate gas exhaust lumen 90 from medial walls 57 of probe 102.

Attention is now drawn to FIG. 5, which presents a simplified schematic of yet another alternative embodiment of the present invention, labeled cryoprobe 103. Construction and operation of cryoprobe 103 is similar to that described in the preceding paragraph, with the exception that in cryoprobe 103 electrical resistance heating is provided by an electrical resistance element 80 positioned proximal to heat exchanging configuration 30, within gas exhaust lumen 90 and in proximity to that portion of gas input lumen 20 which is also positioned within gas exhaust lumen 90. Electrical heating of resistance coil 80 serves to heat gas passing through that portion of gas input lumen 20 contained in gas exhaust lumen 90 of cryoprobe 103.

As may be seen from the discussion hereinabove, FIG. 2 presents an embodiment wherein an electrical resistance heater is positioned within expansion chamber 58 of a cryoprobe, and FIGS. 2-5 present various embodiments wherein an electrical resistance heating element is positioned in proximity to a portion of a gas input lumen 20 through which, during a heating phases of operation of a cryoprobe, gas flows towards operating tip 63. It is to be understood that the specific examples provided by FIGS. 2-5 are meant to be illustrative only, and are not to be construed as limiting. The embodiments presented hereinabove have in common electrical resistance heating elements operable to heat gas either within or flowing towards an operating tip 63, thereby heating operating tip 63. Preferably, for simplicity of construction, low-pressure gas so heated is directed through orifice 40.

Figure 6:
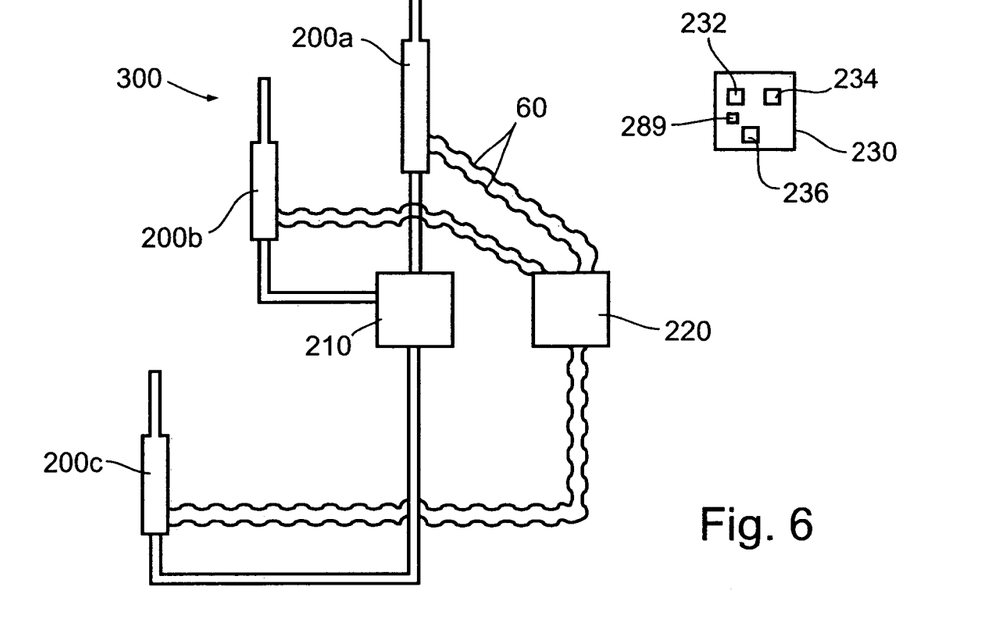
FIG. 6 is a cryoablation system incorporating a cryoprobe coolable by Joule-Thomson cooling and heatable by electrical resistance heating.

Attention is now directed to FIG. 6, which presents a cryoablation system 300 incorporating a cryoprobe 200 coolable by Joule-Thomson cooling and heatable by electrical resistance heating.

Cryoprobe 200 in system 300 may be any one of cryoprobes 100, 101, 102, and 103 presented hereinabove, or any similar cryoprobe having an electrical heating element operable to heat gas within, or flowing towards, operating tip 63.

System 300 includes cryoprobe 200, a gas supply module 210 operable to supply high and low pressure gas to cryoprobe 200, and a power supply module 220 operable to supply power to power leads 60 of cryoprobe 200. Preferably, system 300 also contains a control module 230 operable to receive temperature information from thermal sensor 69 within cryoprobe 200, from other optional thermal sensors, from pressure sensors, and/or from gas flow sensors positioned at various positions in system 300. Preferably, control module 230 contains a memory 232 for storing operating data of system 300, pre-set operational commands, and programmed algorithms for controlling system 300. Preferably, control module 230 also contains an interface device 234 from which a user can receive information concerning operation of system 300, and through which the user can input user commands to control module 230 and thereby control various performance parameters of system 300. System 300 further optionally includes input devices 236 operable to receive input information, either manually or automatically, from external sensors of various sorts. These input devices may include thermocouples or other temperature measurement devices, gas inlet pressure and gas outlet pressure measurement devices, voltage and current information derived from power supply module 220, and information on the estimated temperature of resistance heating elements within probe 200, estimated by evaluation of changes in electrical current and/or voltage as a function of temperatures of the resistance heating elements.

Control of heating and thawing processes within probe 200 may thus be based on feedback measurements of observed or estimated temperatures within or around probe 200, as compared to desired temperature profiles requested by a surgeon using interface device 234 or commanded by command profiles stored in memory 232. Data input devices 236 may include information gleaned from output of Ultrasound, MRI, CT or any other imaging devices, whether interpreted manually or algorithmically.

Cooling and heating of probe 200, or processes of cooling alone or of heating alone, can be activated and controlled by control module 230 according to manually commands and/or automatically according to stored commands or under algorithmic control.

System 300 optionally includes a plurality of cryoprobes 200, here labeled 200a, 200b and 200c. Each probe of this plurality of probes is preferably individually connected to gas source 210 and power source 220, and is individually controllable by control module 230.

Figure 7:
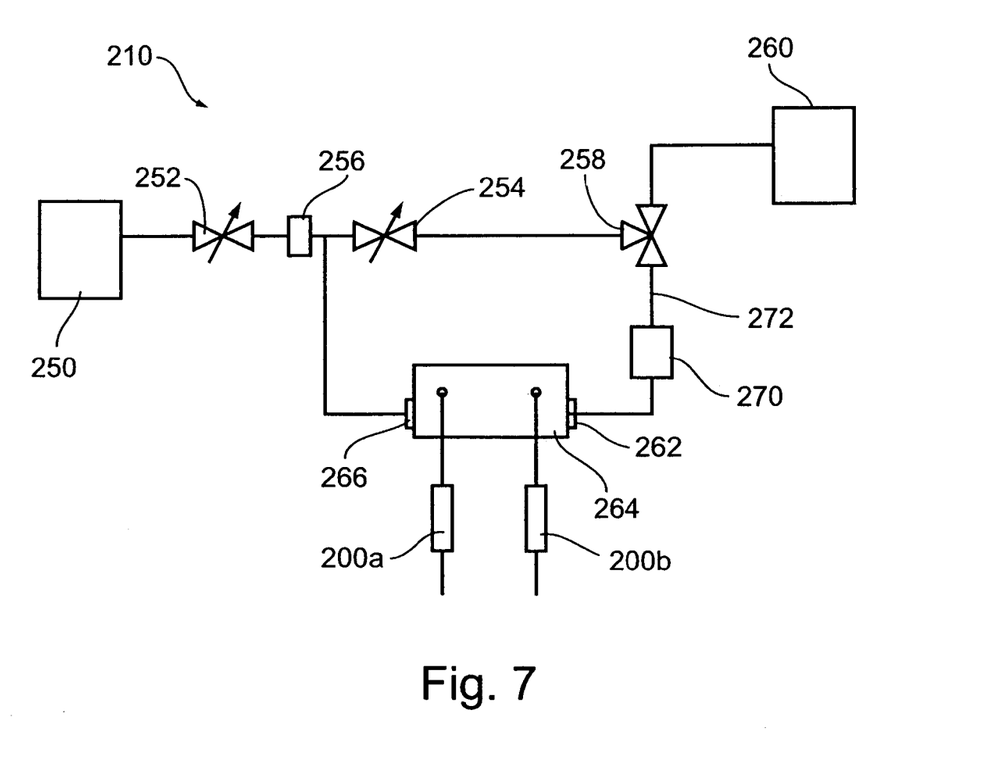
FIG. 7 is a gas supply module, according to a preferred embodiment of the present invention.

Attention is now drawn to FIG. 7, which presents a preferred implementation of gas supply module 210, according to a preferred embodiment of the present invention.

The embodiment of gas supply module 210 presented in FIG. 7 enables selectable utilization of either traditional (prior art) heating by Joule-Thomson heating utilizing high-pressure heating gas, or electrical heating of low-pressure cooling gas directed towards operating tip 63 of probe 200. FIG. 7 presents a cooling gas source 250, which will typically be compressed argon tank commercially available at 6000 psi. A first pressure regulator 252 reduces cooling gas pressure to approximately 3000-4500 psi, which pressure is appropriate for cooling-phase operation of cryoprobe 200. A second pressure regulator 254 further reduces cooling gas pressure to a low pressure, preferably in a range of 200-1000 psi and most preferably in a range of 300-600 psi. A flow sensor 256 is provided to give flow feedback to control module 230, enabling control module 230 to cut off electrical heating power to cryoprobe 200 in the event of a failure of flow of low-pressure cooling gas during a heating phase of operation of cryoprobe 200. (A flow of between 100 and 150 standard liters per minute is currently, considered optimal for this operation.)

Low-pressure cooling gas is thus delivered to a three-way valve 258, preferably a solenoid valve, which also receives gas input from a high-pressure heating gas supply 260, typically a supply of compressed helium at 2500-4000 psi. Thus, three-way valve 258 is operable to select either high-pressure helium (or other heating gas) or low-pressure argon (or other cooling gas) for delivery to a gas-for-heating input 262 of a gas distribution manifold 264. As shown in the figure, high pressure cooling gas is delivered to gas-for-cooling input 266 of gas distribution manifold 264. Gas distribution manifold 264 is operable to selectively connect each of a plurality of cryoprobes 200 either to cooling gas, from gas-for-cooling input 266, or to whatever gas is supplied (according to the setting of three-way valve 258) to gas-for-heating input 262. Pressure gauge 270, on gas-for-heating line 272 connected at 262, provides system feedback to control module 230 by reporting pressure in gas-for-heating line 272, which pressure will be on the order of 2500-4000 psi if three-way valve 258 is set for heating-gas heating, and on the order of 200-1000 psi if three-way valve 258 is set for electrical heating of a low-pressure flow of cooling gas.

Figure 8:
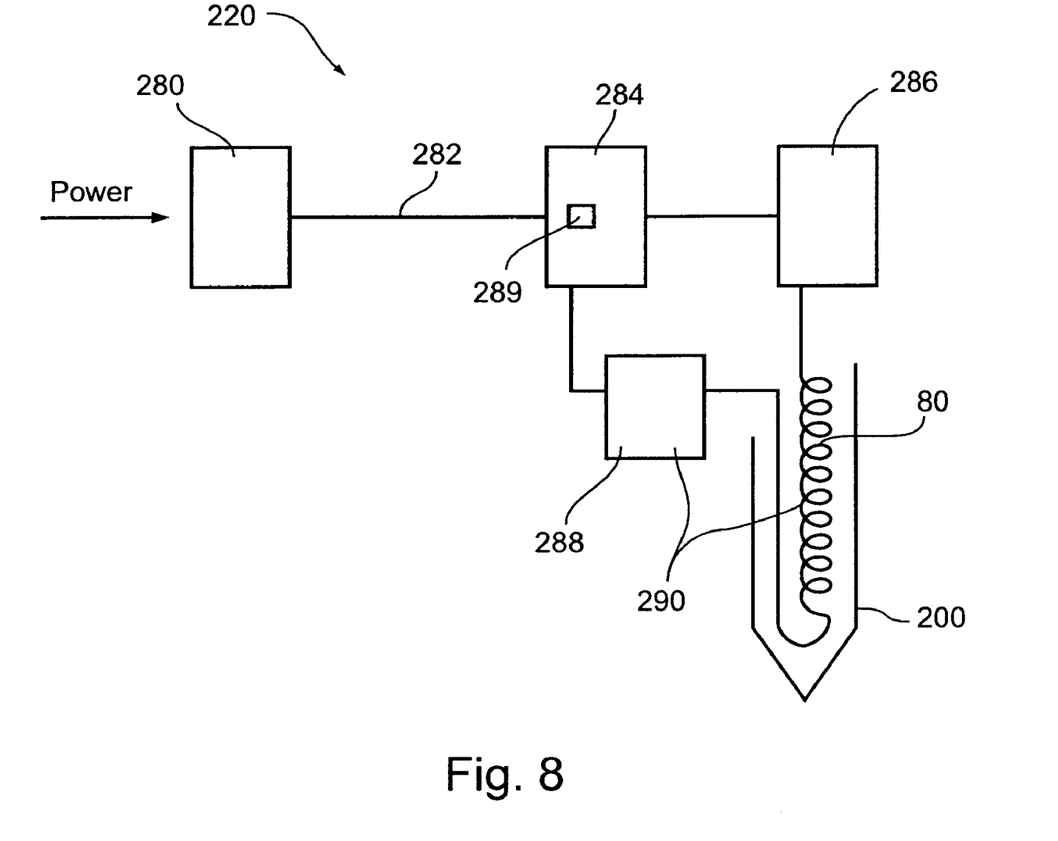
FIG. 8 is a simplified schematic of a power supply module, according to a preferred embodiment of the present invention.

Attention is now drawn to FIG. 8, which presents a simplified schematic of a power supply module, according to a preferred embodiment of the present invention.

Power supply 220 receives power from standard electrical supply sources. Standard power is converted through isolating transformer 280 to 8 volts, provided over several 5-Amp supply lines 282. These lines feed power to a controller switchboard 284, which feeds power through a power board 286 to heating elements 80 within individual cryoprobes 200. Current to individual probes 200 is sensed by current sensors 288, which information is fed back to controller 284. Control module 230 (shown in FIG. 6), including user interface device 234 and other control components described hereinabove, monitors and controls the power delivered to cryoprobes 200. Information about temperatures of probes 200 and current drawn by probes 200 may be displayed on interface device 234.

Current sensors 288 combined with heating elements 80 provide additional functionality as a combined flow-sensing module 290. Heating elements 80 are constructed of electrical resistance materials having a known relationship between their physical temperature and their electrical resistance. According to well-known physical principles, changes in temperature of heating elements 80 result in changes in resistance of those elements. However, as is well known in the art, given a known voltage (optionally, a constant voltage) supplied across resistance heating element 80, and given a current sensor 288 connected in series to resistance element 80, it is possible to calculate in real time the resistance of element 80, as a function of voltage across, and current through, element 80. From that calculated resistance value, knowing the physical characteristics of the material of which element 80 is constructed, it is further possible to calculate the temperature of element 80 as a function of its electrical resistance, itself a function of known or measurable voltage across, and current through, resistance element 80. Thus, information provided by current sensor 288 can be used to calculate the temperature of element 80 at any given moment.

Temperature of heating elements 80 may be taken, in turn, to be fan indication of gas flow within gas input lumen 20 of probe 200. As explained above, gas flowing through gas input lumen 20 is heated by element 80 during heating phase of operation of probe 200. Naturally, the process of heating gas in gas input lumen 20 has the consequential effect of cooling element 80. Control elements located within power supply controller 284 or general control module 230 are operable to make the calculations described in this and the preceding paragraph, and to control operation of power supply 220 and/or of gas supply 210, taking into account the calculated values. Thus, in one embodiment, flow of gas into probes 200 may be adjusted so as to obtain an optimal heating temperature at elements 80. In an alternative embodiment, voltage applied to elements 80 may be modified so as to obtain an optimal heating temperature at elements 80. In a further alternative embodiment, both voltage applied to elements 80 and flow of gas into probes 200 may be modified so as to obtain an optimal heating temperature at elements 80.

In a particularly preferred embodiment, calculations as described in this and the preceding paragraph enable use of flow sensing module 290 to provide a safety cut-off switch 289 operable to protect patients from possible overheating of probes 200: should gas flow in gas input lumen 20 of a probe 200 be impeded or stopped, (if, for example, impurities in the gas clog gas lumen 20 or orifice 40) temperatures of heating elements 80 will rise because of the cessation of gas-flow-based cooling thereof. This rise in temperature will immediately express itself as a change in the resistance of elements 80, which is immediately detectable as a change in the current detected by current sensor 288. Such a change in detected current can then be used to trigger a safety switch 289 (preferably in power supply controller 284 or in general control module 230), which switch 289 will immediately cut off power to heating elements 80, thereby preventing overheating of probes 80, and thereby protecting patients from tissue damage which might otherwise be caused by an overheated probe 200.

In a preferred embodiment of the present invention, probe(s) 200 and elements of system 300 proximate to probe 200 are designed and constructed to be useable within the magnetic field of an MRI environment. In particular, probes 200 are preferably constructed of materials unresponsive to strong magnetic fields, materials such as titanium and inconel. Such materials are not subject to forces which would be induced by an MRI magnet in a probe made, for example, of steel or other traditional cryoprobe materials.

Since cryoprobes made of titanium or inconel or similar materials are not subject to magnetically induced forces, they may be used by a surgeon operating within an MRI magnetic field. For the same reason, probes constructed of such materials will not interact with magnetic or electromagnetic fields in and around the patient, and consequently will not have a deleterious effect on MRI imaging of a patient during cryosurgery.

Portions of gas supply system 210 proximate to cryoprobes 200, such as gas input and exhaust lines connected to cryoprobes 200, are preferably also constructed of materials uninfluenced by the MRI magnetic field. Similarly, portions of electrical system 220 within or near probes 200, and portions of control system 230 within or near probes 200, are also designed and constructed so as to be uninfluenced by the strong magnetic fields produced by MRI imaging equipment, and to not influence the magnetic field responses detected by MRI imaging equipment. Electrical elements, in particular, are preferably shielded by several layers of μ-metal (mu-metal) having high electro-magnetic permeability, which shield is grounded at close intervals to minimize conduction paths for induced currents. Thus equipped, probes 200 and system 300 are compatible for use in real-time MRI-guided cryosurgery applications.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A cryotherapy apparatus, comprising:
   (a) a gas source operable to deliver both a high-pressure cooling gas and a low-pressure gas to a cryoprobe;
   (b) a cryoprobe having a gas input conduit, an operating tip which comprises a Joule-Thomson orifice, an expansion chamber, and an electrical heating element positioned to heat flowing input gas when gas is supplied by said gas source and caused to flow through said gas input conduit, said orifice, and said expansion chamber;
   (c) a power source operable to deliver electrical power to said heating element when commended to do so by a controller; and
   (d) a controller operable to switch between
      (i) a heating mode in which said gas source delivers low-pressure gas to said cryoprobe and said power source delivers electrical power to said heating element, and
      (ii) a cooling mode in which said gas source delivers high-pressure gas to said cryoprobe and said power source does not deliver electrical power to said heating element.

2. The apparatus of claim 1, wherein said electrical resistance heating element is positioned within said operating tip.

3. The apparatus of claim 1, wherein said electrical resistance heating element is positioned within said cryoprobe and external to said operating tip.

4. The apparatus of claim 1, wherein said heating element is in direct contact with said flowing low-pressure gas during said heating.

5. The apparatus of claim 4, wherein said electrical resistance heating element is operable to heat gas flowing within said gas input lumen.

6. The apparatus of claim 1, wherein said low-pressure gas is low-pressure cooling gas.

7. A cryotherapy apparatus useable to cryoablate tissue of a body, comprising
   (a) a gas supply operable to supply both high-pressure cooling gas and a low-pressure gas;
   (b) a cryoprobe having an operating tip which includes a Joule-Thomson orifice and an expansion chamber, which operating tip is operable to be cooled by expansion of high-pressure cooling gas from said gas supply delivered through said orifice and expanding in said expansion chamber, and wherein said operating tip further comprises an electrical resistance heating element positioned within said expansion chamber and operable to electrically heat low-pressure gas from said gas supply delivered through said orifice and flowing within said expansion chamber; and (c) a controller supplying power to said electrical resistance element while said gas supply supplies said low-pressure gas.

8. A cryotherapy apparatus comprising a cryoprobe which comprises:

(a) an operating tip which comprises an expansion chamber;

(b) a gas input lumen having at its distal end a Joule-Thomson orifice positioned between said gas input lumen and said expansion chamber;

(c) an electrical resistance heater so positioned and configured that if low-pressure gas is caused to flow through said gas input lumen towards and through said orifice while electric power is supplied to said electrical resistance heater, gas flowing into said expansion chamber is sufficiently heated by said resistance heater to heat said tip sufficiently to thaw frozen body tissues adjacent to said tip; and (d) a controller configured to command supplying of low-pressure gas to said gas input lumen and to command supplying of electric power to said electrical resistance heater during said supplying of low-pressure gas to said gas input lumen.

9. The apparatus of claim 8, further comprising a gas supply operable to selectively supply either a high-pressure cooling gas or a low-pressure gas to said gas input lumen according to commands received from said controller.

10. The apparatus of claim 9, wherein said gas supply is further operable to supply a high-pressure heating gas.

11. The apparatus of claim 9, wherein said gas supply supplies only a single type of gas, and said single type of gas is selectively supplied at low or at high pressure.

12. The apparatus of claim 9, wherein said low-pressure gas is air.

13. The apparatus of claim 8, wherein said electrical resistance heating element is proximate to a portion of said gas input lumen and is operable to heat gas flowing within said gas input lumen.

14. The apparatus of claim 8, wherein said cryoprobe further comprises a thermal sensor.

15. The cryoprobe of claim 14, wherein said thermal sensor is a thermocouple.

16. The apparatus of claim 8, wherein said cryoprobe further comprises a heat-exchanging configuration which comprises said electrical resistance heating element.

17. The apparatus of claim 16, wherein said heat-exchanging configuration comprises a portion of said gas input lumen which is spirally wrapped around a central core.

18. The apparatus of claim 8, wherein a portion of said a gas input lumen of said cryoprobe is spirally wrapped around a central core, and said central core comprises said electrical resistance heating element.

19. The apparatus of claim 8, wherein said cryoprobe comprises a gas exhaust lumen containing said electrical resistance heating element and a portion of said gas input lumen.

20. The apparatus of claim 8, wherein said cryoprobe comprises a gas exhaust lumen, at least a portion of said gas input lumen is contained within said gas exhaust lumen, and said electrical resistance heating element is external to, and contiguous to, said gas exhaust lumen.

21. A cryotherapy apparatus comprising:

(a) a gas supply operable to supply both high-pressure cooling gas and a low-pressure gas; and (b) a cryoprobe which comprises (i) a single gas input lumen operable to direct gas from said gas supply to a Joule-Thomson orifice in an operating tip of said probe; and (ii) an electrical resistance heating element operable to heat gas directed through said gas input lumen toward said orifice; and (c) a controller configured to coordinate supplying of gas and heating of said heating element in such manner that said resistance heating element heats during supplying of low-pressure gas and not during supplying of high-pressure gas.

22. A system for cryoablating tissue, comprising:

(a) A cryoprobe useable to cryoablate tissue of a body, which cryoprobe comprises an operating tip which includes a Joule-Thomson orifice, which operating tip is operable to be cooled by expansion of high-pressure cooling gas through said orifice, and wherein said operating tip is further operable to be heated by flowing heated low-pressure gas directed to said operating tip;

(b) a gas supply operable to supply high-pressure cooling gas to said cryoprobe and also operable to supply low-pressure cooling gas to said cryoprobe;

(c) a power supply operable to supply electric power to a resistance element operable to heat a flow of low-pressure cooling gas; and (d) a controller configured to command said power supply to supply electric power to said resistance element only during times when said gas supply is supplying low-pressure gas to said cryoprobe.

23. The system of claim 22, wherein said resistance element is positioned within said cryoprobe.

24. The system of claim 22, wherein said resistance element is positioned within said operating tip.

25. The system of claim 22, wherein said resistance element is positioned within an expansion chamber contiguous to said orifice.

26. The system of claim 22, wherein said cryoprobe further comprises a heat exchanging configuration, and said heat exchanging configuration comprises said resistance element.

27. The system of claim 22, wherein said gas supply is further operable to supply high-pressure heating gas to said cryoprobe.

28. The system of claim 22, further comprising a control module operable to influence temperatures of said cryoprobe by regulating output of at least one of a group consisting of said power supply and said gas supply.

29. The system of claim 22, further comprising a control module operable to influence temperatures of said cryoprobe by regulating output of said power supply and by regulating output of said gas supply.

30. The system of claim 22, further comprising a current sensor and a power cut-off switch operable to cut power to said resistance element when current detected by said current sensor indicates that said resistance element has heated beyond a predetermined threshold.

31. The system of claim 22, further comprising a current sensor and a power cut-off switch operable to cut power to said resistance element when current detected by said current sensor falls below a predetermined threshold.

32. The system of claim 22, wherein said control system is operable to calculate an operational command for said power supply based on algorithmic analysis of data obtained from a thermal sensor.

33. The system of claim 32, wherein thermal sensor is a thermocouple.

34. The system of claim 22, wherein said control system is operable to calculate an operational command for said power supply based on algorithmic analysis of data obtained from a pressure sensor.

35. The system of claim 22, wherein said control system is operable to calculate an operational command for said power supply based on algorithmic analysis of data obtained from a current sensor.

36. The system of claim 22, wherein said control system is operable to calculate an operational command for said power supply based on algorithmic analysis of data obtained from a gas flow sensor.

37. The system of claim 36, wherein said gas flow sensor comprises an electrical resistance heating element whose resistance varies as a function of its temperature, and a current sensor operable to measure current flowing through said electrical resistance heating element.

38. The system of claim 22, wherein said cryoprobe is constructed of MRI-compatible material.

39. The system of claim 38, wherein said MRI-compatible material is selected from a group consisting of titanium and inconel.

40. The system of claim 38, wherein electrical components within and proximate to said cryoprobe are shielded with Mu-metal.

41. A method for using a cryoprobe to cryoablate tissues at a cryoablation target site within a body and for subsequently disengaging said cryoprobe from said cryoablation site, comprising:
  (a) positioning a cryoprobe operating tip which comprises a Joule-Thomson orifice and an expansion chamber in a vicinity of a cryoablation target site;
  (b) cooling said operating tip to cryoablation temperatures by passing high-pressure cooling gas through said orifice, causing said cooling gas to expand in said expansion chamber, thereby cooling said operating tip, thereby cryoablating tissues at said cryoablation target site; and
  (c) using a controller to coordinate causing a low-pressure gas to flow through said Joule-Thomson orifice while utilizing an electrical resistance heating element within said cryoprobe to heat said flowing low-pressure gas, thereby heating said operating tip, thereby thawing tissues contiguous to said operating tip;
    thereby cryoablating tissue at said cryoablation target site and subsequently disengaging said cryoprobe from said cryoablation target site.

42. The method of claim 41, further including utilizing said electrical resistance heating element to heat a flow of gas directed through a gas input lumen to said operating tip.

43. The method of claim 41, further including utilizing said electrical resistance heating element to heat a flow of gas directed through a gas input lumen to a Joule-Thomson orifice in said operating tip.

44. A power cut-off system for a cryoprobe, comprising:
  (a) an electrical resistance heating element for heating an operating tip of a cryoprobe;
  (b) a current detector operable to report a measure of current passing through said electrical resistance heating element when said electrical resistance heating element is used to heat said operating tip;
  (c) a power supply operable to supply power to said electrical resistance heating element; and
  (d) a power cut-off switch operable to cut off power flow from said power supply to said electrical resistance element when said current detector detects a current inferior to a predetermined value.

\* \* \* \* \*